(12) United States Patent
Davé

(10) Patent No.: US 8,617,470 B2
(45) Date of Patent: Dec. 31, 2013

(54) SYSTEM FOR LABEL-FREE QUANTITATIVE DETECTION OF BIOMOLECULES

(75) Inventor: Digant P. Davé, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 50 days.

(21) Appl. No.: 12/943,925

(22) Filed: Nov. 10, 2010

(65) Prior Publication Data

US 2011/0171072 A1    Jul. 14, 2011

Related U.S. Application Data

(60) Provisional application No. 61/259,731, filed on Nov. 10, 2009.

(51) Int. Cl.
*G01N 33/00*    (2006.01)

(52) U.S. Cl.
USPC ................... 422/82.11; 422/68.1; 422/500

(58) Field of Classification Search
USPC ..................... 422/82.11, 68.1, 500
See application file for complete search history.

(56) References Cited

U.S. PATENT DOCUMENTS

2008/0316485 A1* 12/2008 Wawro et al. ............. 356/328

OTHER PUBLICATIONS

Belmont, et al., "Molecularly imprinted polymer films for reflectometric interference spectroscopic sensors," *Biosens. Bioelectron.*, 22:3267-72, 2007.
Birkett and Gauglitz, "Development of an assay for label-free high-throughput screening of thrombin inhibitors by use of reflectometric interference spectroscopy," *Analytical Bioanalytical Chemistry*, 372:141, 2002.
Birkett, et al., "Label-free parallel screening of combinatorial triazine libraries using reflectometric interference spectroscopy," *Anal. Chem.*, 74:834-40, 2002.
Bornhop, et al., "Free-solution, label-free molecular interactions studied by back-scattering interferometry," *Science*, 317:1732-6, 2007.
Brecht and Gauglitz, "Recent development in optical transducers for chemical or biochemical applications," *Sensors and Actuators B*, 38-39:1-7, 1997.
Chaerkday and Pandey, "Quantitative proteomics for identification of cancer biomarkers," *Proteomics Clin. Appl.*, 1:1080-9, 2007.
Choma, et al., "Sensitivity advantage of swept source and Fourier domain optical coherence tomography," *Opt. Express*, 11:2183-9, 2003.

(Continued)

*Primary Examiner* — Sam P Siefke
(74) *Attorney, Agent, or Firm* — Fulbright & Jaworski, LLP

(57) ABSTRACT

Embodiments of apparatuses, systems, and methods for label-free detection of biomolecules. In one embodiment, a system includes a light source configured to emit broadband Gaussian light. The system may also include an optical fiber coupled to the light source. Additionally, the system may include an optical sensor. The optical sensor may include a fiber-interface surface configured to be coupled to the optical fiber and to receive broadband Gaussian light from the optical fiber. The optical sensor may also include a sensor body coupled to the fiber-interface surface, the sensor body having a refractive index different from a refractive index of the optical fiber, such that at least a portion of light received by the fiber-interface surface is reflected back to the optical fiber during use; and a binder-interface surface coupled to the sensor body, the binder-interface surface configurable to receive a chemical binder layer. Additional embodiments include coherence domain multiplexing and time division multiplexing.

12 Claims, 12 Drawing Sheets

(56) References Cited

OTHER PUBLICATIONS

Choma, et al., "Spectral-domain phase microscopy," *Opt. Lett.*, 30:1162-4, 2005.
Cross, et al., "A new quantitative optical biosensor for protein characterization," *Biosens. Bioelectron.*, 19:383-90, 2003.
Davé and Chirvi, "Label-free quantitative detection of biomarkers," *Progress in Biomedical Optics and Imaging*, 11, 2010.
Davé, "Phase sensitive interferometry for biosensing applications," *Methods Mol. Biol.*, 503:179-87, 2009.
de Boer, et al., "Improved signal-to-noise ratio in spectral-domain compared with time-domain optical coherence tomography," *Opt. Lett.*, 28:2067-9, 2003.
Dong and Shannon, "Heterogeneous immuno sensing using antigen and antibody monolayers on gold surfaces with electrochemical and scanning probe detection," *Anal. Chem.*, 72:2371-6, 2000.
Easley, et al., "Extrinsic Fabry-Perot interferometry for noncontact temperature control of nanoliter-volume enzymatic reactions in glass microchips," *Anal. Chem.*, 77:1038-45, 2005.
Hast, et al., "Direct optical biosensor, based on optical feedback interferometry," *IEEE*, 177, 2005.
Joo and de Boer, "Spectral-domain optical coherence reflectometric senor for highly sensitive molecular detection," *Optics Letters*, 32:2426-8, 2007.
Joo, et al., "Spectral-domain optical coherence phase microscopy for label-free multiplexed protein microarray assay," *Biosensors and Bioelectronics*, 25:275-81, 2009.
Joo, et al., "Spectral-domain optical coherence phase microscopy for quantitative phase-contrast imaging," *Optics Letters*, 16:2131-3, 2005.
Kinrot and Nathan, "Investigation of a periodically segmented waveguide Fabry-Pérot interferometer for use as a chemical/biosensor," *Journal of Lightwave Technology*, 24:2139, 2006.
Kröger, et al., "Epitope-mapping of transglutaminase with parallel label-free optical detection," *Biosens. Bioelectron.*, 17:937-44, 2002.
Leitgeb, et al., "Performance of fourier domain vs. time domain optical coherence tomography," *Opt. Express*, 11:889-94, 2003.
Lin, et al., "A porous silicon-based optical interferometric biosensor," *Science*, 278:840-3, 1997.
Lu, et al., "Reflective interferometric detection of label-free oligonucleotides," *Anal. Chem.*, 76:4416-20, 2004.
Markov, et al., "Label-free molecular interaction determinations with nanoscale interferometry," *J. Am. Chem. Soc.*, 126:16659-64, 2004.
Möhrle, et al., "Label-free characterization of cell adhesion using reflectometric interference spectroscopy (RIfS)," *Anal. Bioanal. Chem.*, 384:407-13, 2005.
Nassif, et al., "In vivo high-resolution video-rate spectral-domain optical coherence tomography of the human retina and optic nerve," *Opt. Express*, 12:367-76, 2004.
Özkumur, et al., "Label-free and dynamic detection of biomolecular interactions for high-throughput microarray applications," *Proc. Natl. Acad. Sci. USA*, 105:7988-92, 2008.
Pacholski, et al., "Reflective interferometric fourier transform spectroscopy: a self-compensating label-free immunosensor using double-layers of porous $SiO_2$," *J. Am. Chem. Soc.*, 128:4250-2, 2006.
Park, et al., "Real-time fiber-based multi-functional spectral-domain optical coherence tomography at 1.3 microm," *Opt. Express*, 13:3931-44, 2005.
Peng, et al., "Adaptive interferometry of protein on a BioCD," *Appl. Opt.*, 46:5384-95, 2007.
Petrou, et al., "Real-time label-free detection of complement activation products in human serum by white light reflectance spectroscopy," *Biosens. Bioelectron.*, 24:3359-64, 2009.
Piehler, et al., "Label-free monitoring of DNA-ligand interactions," *Anal. Biochem.*, 249:94-102, 1997.
Pröll, et al., "Label-free characterisation of oligonucleotide hybridisation using reflectometric interference spectroscopy," *Anal. Bioanal. Chem.*, 382:1889-94, 2005.
Proll, et al., "Potential of label-free detection in high-content-screening applications," *J. Chromatogr. A.*, 1161:2-8, 2007.
Rich and Myszka, "Higher-throughput, label-free, real-time molecular interaction analysis," *Anal. Biochem.*, 361:1-6, 2007.
Schmitt, et al., "Development of a highly sensitive interferometric biosensor," *Proceedings of SPIE*, 5461:22, 2004.
Schmitt, et al., "Interferometric biosensor based on planar optical waveguide sensor chips for label-free detection of surface bound bioreactions," *Biosens. Bioelectron.*, 22:2591-7, 2007.
Schneider, et al., "Hartman interferometer: versatile integrated optic sensor for label-free, real-time quantification of nucleic acids, proteins, and pathogens," *Clin. Chem.*, 43:1757-63, 1997.
Vakhtin, et al., "Common-path interferometer for frequency-domain optical coherence tomography,".
Varma, et al., "High-speed label-free detection by spinning-disk micro-interferometry," *Biosens. Bioelectron.*, 19:1371-6, 2004.
Varma, et al., "Spinning-disk self-referencing interferometry of antigen-antibody recognition," *Opt. Lett.*, 29:950-2, 2004.
Zhang, et al., "Observing interactions between the IgG antigen and anti-IgG antibody with AFM," *IEEE Eng. Med. Biol. Mag.*, 16:42-6, 1997.

\* cited by examiner

SYSTEM FOR LABEL-FREE QUANTITATIVE DETECTION OF BIOMOLECULES

RELATED APPLICATIONS

This application claims priority to U.S. Provisional Application No. 61/259,731, filed Nov. 10, 2009, the entire contents of which is incorporated herein by reference.

BACKGROUND OF THE INVENTION

1. Field of the Invention

This invention relates to spectrometry and more particularly relates to an apparatus, system, and method for label-free quantitative detection of biomarkers.

2. Description of the Related Art

Biomarker detection plays an important role in the diagnosis of various diseases, life science research and drug discovery. Detection and quantification of these biomarkers have the potential of improving and expediting drug development, treatment planning, and prediction of reoccurrence of various diseases. It can provide an important diagnostic tool at the molecular level. For example, cancer cells typically over express biomarkers as compared to their non-tumorogenic counterparts. Hence, the quantification of biomarkers often plays an important role in differentiating cancerous cells from non-cancerous cells.

Additionally, current methods for studying protein-analyte interactions or detecting a specific protein include enzyme-linked immunosorbent assays (ELISA) and western blotting. These long established techniques, however, need secondary probes for detection of analytes that may alter the protein of interest, are relatively costly, and require extensive sample preparation. On the other hand, researchers are exploring different label-free techniques for the detection and quantification of protein-analyte interaction. Some of the techniques explored are Isothermal Titration Calorimetry (ITC), Differential Scanning calorimetry (DSC), and ellipsometry imaging, among others. Using these techniques, binding affinity of analyte to protein, kinetic characterization, and protein quantization can be achieved.

The detection and quantification of large and small molecules is necessary in a wide variety of fields ranging from biosensing to screening of biomolecules in the drug discovery process. Currently, the technologies that are predominantly used in practice are label-based in which biomolecules to be screened are labeled with fluorescent, radioisotope, or chemiluminescent tags. Inherent limitations of labels are widely acknowledged, the most important of which center on their potential interference with the activity of the biomolecule and its interaction with the recognition molecule, along with the added costs involved in developing and implementing the label attachment chemistry. Furthermore, direct quantification of interactions and concentrations are not possible using labeled methods. Label-free detection and quantification of bimolecular interaction has significant advantages, such as lack of interference from labels, higher accuracy and less expensive assays. Until recently, surface plasmon resonance (SPR) was perhaps the only reliable and widely used label-free technique due to the sensitivity and commercial availability of the instrumentation. But, for multi-analyte detection, SPR has achieved limited success.

In recent years a number of promising label-free techniques have been developed that have the potential to be the method of choice for a number of biomolecular interaction analysis applications. Using label-free optical techniques, either the change in refractive index (RI) or the change in optical path length (OPL-a product of geometric length and RI) that occurs when biomolecules bind to the target is measured. Changes in RI or OPL can be accurately measured with optical techniques such as interferometry and SPR. Besides detection sensitivity, high throughput is necessary and is an important figure of merit for many biosensing applications. Limited throughput capability is a drawback of typical label-free techniques such as SPR. Although high throughput label-free detection of biomolecules has been demonstrated using spin-disk interferometry and spectral reflectance imaging of biosensor arrays, these techniques are limited to fixed biosensor formats with custom fabricated biosensor substrates.

SUMMARY OF THE INVENTION

Embodiments of an optical sensor are presented. In one embodiment, the optical sensor includes a fiber-interface surface configured to be coupled to an optical fiber and to receive broadband Gaussian light from the optical fiber. The optical sensor may also include a sensor body coupled to the fiber-interface surface, the sensor body having a refractive index different from a refractive index of the optical fiber such that at least a portion of light received by the fiber-interface surface will be reflected back to the optical fiber during use; and a binder-interface surface coupled to the sensor body, the binder-interface surface configured to receive a chemical binder layer.

In a further embodiment, the optical sensor may include a binder layer comprising a first molecule configured to molecularly bind to a second molecule. In such an embodiment, an optical path distance of the optical sensor will increase in response to the second molecule binding to the first molecule.

In one embodiment, the sensor body may include glass. Alternatively, the sensor body may include plastic. In still another embodiment, the sensor body may include sapphire. In another embodiment, the sensor body may include a metallic layer, and a segment of an optical fiber. The metallic layer may be disposed between the optical fiber and the segment of an optical fiber. The length of the segment of the optical fiber may be selected according to a desired optical path length for the optical sensor. In one embodiment, the metallic layer may be silver. Alternatively, the metallic layer may be gold, chromium, aluminum, or other suitable materials. In these examples, the sensor body may have a physical thickness in the range of 100 µm to 1.5 mm. Alternatively, the thickness of the sensor body may be as great as 15 mm if the wavelength of the light source and resolution of the spectrometer are selected to accommodate such thicknesses. Other suitable sizes and materials will be apparent to those of ordinary skill in the art.

Another embodiment of an optical sensor includes a housing. The housing may be configured to receive at least a portion of an optical fiber. This embodiment may also include a ferrule configured to retain the portion of the optical fiber within the housing. Additionally, this embodiment may include a lens disposed within the housing and configured to collimate light received from the optical fiber and to focus light reflected to the optical fiber. The lens may be a gradient-index ("GRIN") lens. Also, the optical sensor may include a sensor member coupleable to the housing, the sensor member being configured to reflect at least a portion of the light that is received from the optical fiber back to the optical fiber. The sensor member may be integrated with the optical sensor or be a distinct item. In a particular embodiment, the sensor member may be disposable. Alternatively, the sensor member may be reusable. In such embodiments, the sensor member may be removable from the housing for cleaning and preparation for reuse.

In some embodiments, the sensor member may include a fiber-interface surface configured to receive broadband Gaussian light from the optical fiber. The sensor member may also include a sensor body coupled to the fiber-interface surface, the sensor body having a refractive index different from a refractive index of the optical fiber such that at least a portion of light received by the fiber-interface surface will be reflected back to the optical fiber during use; and a binder-interface surface coupled to the sensor body, the binder-interface surface configured to receive a chemical binder layer.

One or more embodiments involve systems. One embodiment of the present systems includes a light source configured to emit broadband Gaussian light. The system may also include an optical fiber coupled to the light source. Additionally, the system may include an optical sensor. The optical sensor may include a fiber-interface surface configured to be coupled to the optical fiber and to receive broadband Gaussian light from the optical fiber. The optical sensor may also include a sensor body coupled to the fiber-interface surface, the sensor body having a refractive index different from a refractive index of the optical fiber such that at least a portion of light received by the fiber-interface surface will be reflected back to the optical fiber during use; and a binder-interface surface coupled to the sensor body, the binder-interface surface configurable to receive a chemical binder layer.

In one embodiment, the system may also include a spectrometer coupled to the optical fiber, and the spectrometer may receive the light reflected by the optical sensor.

The system may also include a plurality of optical couplers, each of which may direct the light reflected by one or more optical sensors to the spectrometer. The system may also include a multiplexer configured to communicate light reflected by a plurality of optical sensors to the spectrometer. The multiplexer may be a time division multiplexer (TDM). For example, the multiplexer may include a galvo configured to scan a plurality of optical fiber inputs. In an alternative embodiment, the multiplexer may include a two dimensional linear translation stage. The multiplexer may be configured to perform a raster scan of a plurality of optical fiber inputs.

In a further embodiment, the system may include one or more sets of optical sensors having at least a first set of optical sensors, each optical sensor in the first set having a unique physical thickness. The system may also include a plurality of optical fibers, each coupled to at least one of the optical sensors in the first set of optical sensors. In such an embodiment, the system may also include a spectrometer coupled to the plurality of optical fibers. The spectrometer may be configured to simultaneously detect light reflected by each optical sensor in the first set of optical sensors, and demultiplex the signals received according to a coherence multiplexing algorithm. This embodiment of the system may also include a TDM coupled to the one or more sets of optical sensors, the TDM configured to communicate light reflected by the each of the sets of optical sensors to the spectrometer within a designated time slot. In a further embodiment, the system may also include a flow cell coupled to the optical sensor, the flow cell configured to direct target materials into contact with the optical sensor.

Other described embodiments may include systems for label-free detection comprising a spectral domain phase sensitive interferometer and a patterned molecularly tailored recognition layer deposited on a plurality of optically clean substrates. In such embodiments, the spectral domain phase sensitive interferometer may include a collimated light from a fiber port that is focused on a sample from a broadband super luminescent diode source coupled to a 2×2 single mode fiber splitter. In a particular embodiment, the fiber port further includes a fiber coupler port terminated with a Ferrule Connector/Angled Physical Contact (FC/APC) connector mounted onto the fiber port. The fiber coupler port further may include an unused port that is angle polished or angle cleaved to avoid back reflection from fiber-air interface into the fiber coupler port.

Other embodiments involve processes for label-free detection. One embodiment of the present processes includes preparing a blank substrate, depositing a molecularly tailored recognition layer on the blank substrate, binding a target biomolecule to the molecularly tailored recognition layer, and measuring a change in optical thickness due to binding of the target biomolecule to the molecularly tailored recognition layer.

Apparatuses for label-free detection are also described. One embodiment of the present apparatuses includes a spectral domain phase sensitive interferometer and a patterned molecularly tailored recognition layer on a plurality of optically clear substrates. The spectral domain phase sensitive interferometer may also include a collimated light from a fiber port that is focused on a sample from a broadband super luminescent diode source coupled to a 2×2 single mode fiber splitter. The fiber port may also include a fiber coupler port terminated with a FC/APC connector mounted onto the fiber port. The fiber coupler port may include an unused port that is angle polished or angle cleaved to avoid back reflection from fiber-air interface into the fiber coupler port.

Although the term "label-free" is used throughout this description, it should not be interpreted as a system that is entirely free of labels. Rather, the term means that although certain embodiments can be used in conjunction with labels, the labels are not required to obtain certain benefits of the embodiments described here.

The term "coupled" is defined as connected, although not necessarily directly, and not necessarily mechanically.

The terms "a" and "an" are defined as one or more unless this disclosure explicitly requires otherwise.

The term "substantially" and its variations are defined as being largely but not necessarily wholly what is specified as understood by one of ordinary skill in the art, and in one non-limiting embodiment "substantially" refers to ranges within 10%, preferably within 5%, more preferably within 1%, and most preferably within 0.5% of what is specified. In any of the embodiments in the present disclosure, the term "substantially" may be substituted with "within [a percentage] of" what is specified, where the percentage includes 0.1, 1, 5, 10, and/or 15 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

Other features and associated advantages will become apparent with reference to the following detailed description of specific embodiments in connection with the accompanying drawings.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION

Various features and advantageous details are explained more fully with reference to the nonlimiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those skilled in the art from this disclosure.

Figure 1:
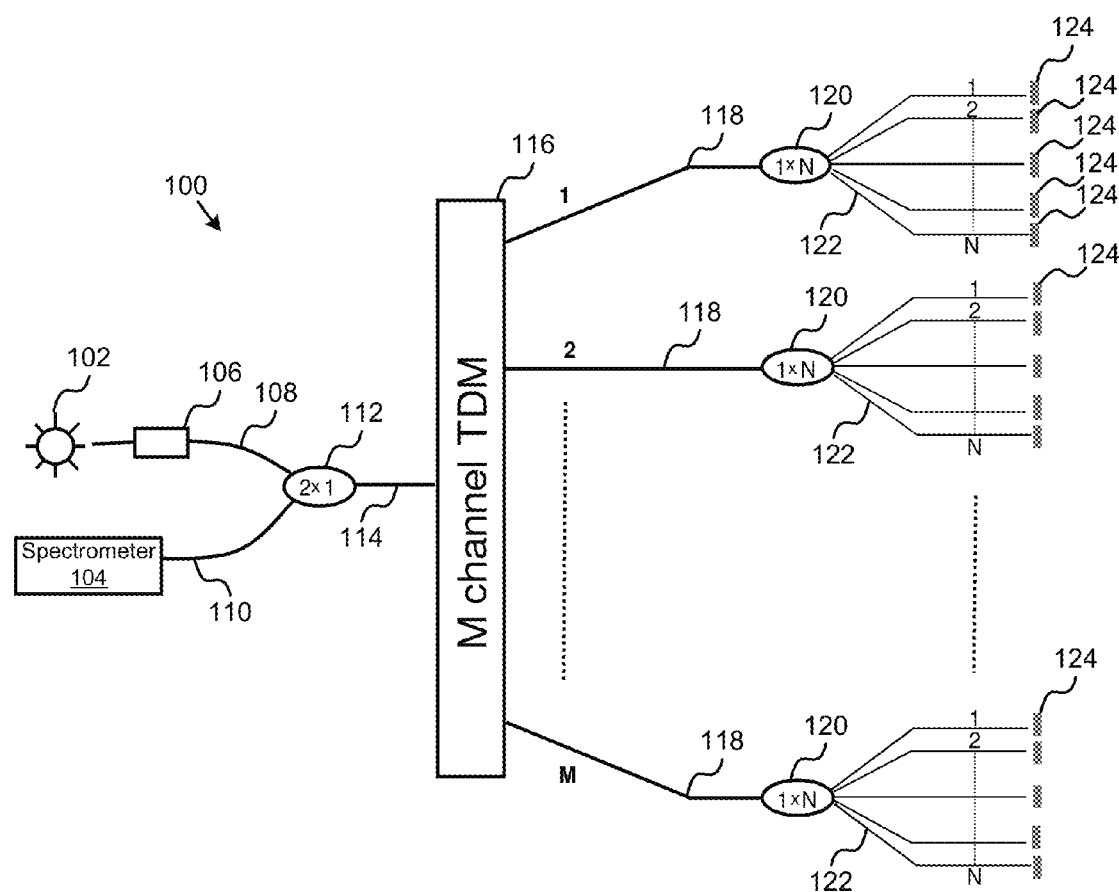
FIG. 1 is a schematic block diagram illustrating one embodiment of a multiplexed label-free spectrometry system configured for both time division multiplexing and coherence multiplexing.

FIG. 1 is a schematic block diagram illustrating one embodiment of a multiplexed label-free spectrometry system 100 configured for both time division multiplexing and coherence multiplexing. In one embodiment, the system 100 may include a light source 102, a spectrometer 104, one or more couplers 112, 120, a multi-channel TDM 116, one or more optical fibers 108, 110, 114, 118, 122, and one or more optical sensors 124.

In one embodiment, the light source 102 may emit broadband Gaussian light. In general, the light source 102 may illuminate an optical sensor 124 by transmitting light through one or more optical fibers 108, 114, 118, 122. In particular, the light spectrum may be shaped, such that the Gaussian band is symmetric about a center wavelength. For example, the light source 102 may be a SLD broadband source (spectrum width 20 nm FWHM) having a center wavelength at 800 nm and coherence length less than 10 μm and a 635 nm guiding beam for visualizing the light beam.

The system 100 may also include a spectrometer 104. The spectrometer 104, may also be coupled to the optical sensor 124. In general, the spectrometer 104 is configured to receive light reflected by the optical sensors 124, and analyze the reflected light to quantify a property sensed by the optical sensor 124. For example, the optical sensor 124 may be configured to capture an antibodies or an analyte, and the light reflected by the optical sensor 124 to the spectrometer may be analyzed by the spectrometer 104 to determine a quantity of the analyte or antibodies captured by the optical sensor 124. In particular, the spectrometer 104 may determine an optical path length of the reflected light, which is proportional to the quantity of antibodies captured by the optical sensor 124. In one embodiment, the spectrometer 104 may be a Common-path interferometer used for highly sensitive detection of change in OPL due to high common mode phase noise rejection afforded by this configuration.

As described above, the system 100 may also include an optical fiber 122 coupled to the light source 102. In various configurations, additional optical fibers 108, 118 may also be coupled to the light source. In certain embodiments, the optical fibers 108, 118, 122 may be coupled by one or more optical couplers 112, 120 or other system components, such as a TDM 116. Additionally, the system 100 may include optical fibers 110, 118, 122 for coupling the spectrometer 104 to one or more optical sensors 124.

The system 100 may also include a plurality of optical couplers 112, 120. Each optical coupler 112, 120 may direct the light to the one or more optical sensors 124 and direct light reflected by one or more optical sensors 124 to the spectrometer 104. Various types of optical coupler may be used. For example, coupler 112 may be a 2×1 coupler, or a 2×2 coupler configured as a 2×1 coupler. In another embodiment, the 2×1 coupler 112 may be replaced by an optical circulator. The couplers 120 between the TDM 116 and the optical sensors 124 may be 1×N optical couplers or 2×N optical couplers, where N is an integer. For example, optical couplers 120 may be a 2×8 optical coupler.

Each optical sensor 124 may receive light from the light source 102, and reflect at least a portion of the light received back through the system 100 to the spectrometer 104.

Embodiments of the optical sensor 124 are described in greater detail below with reference to FIGS. 2-4.

The system 100 may also include a multiplexer 116 configured to communicate light reflected by a plurality of optical sensors 124 to the spectrometer 104. For example, the multiplexer may be a TDM 116 as illustrated in FIG. 1. In one embodiment, the multiplexer 116 may include a galvo configured to scan multiple inputs from optical fibers 118. In an alternative embodiment, the multiplexer 116 may include a two dimensional linear translation stage. The multiplexer 116 may be configured to perform a raster scan of a plurality of optical fiber inputs. Further embodiments of the multiplexer 116 are described in FIGS. 6A and 6B.

By way of example, the system 110 illustrated in FIG. 1 may operate according to the following embodiment. A braoadband Gaussian light source 102 may be coupled to a 2×1 coupler 112 by a optical fiber 108. Additionally, a spectrometer 104 may be coupled to the 2×1 coupler 112 by a second optical fiber 110. To prevent cross-communication of light between the light source 102 and the spectrometer 104, an optical isolator 106 may be included. The 2×1 coupler 112 may be connected to an eight channel TDM 116.

Additionally, this embodiment may include eight sets of optical sensors. Each set may contain four individual optical sensors 124. Each optical sensor 124 in a set may be coupled to a 1×4 coupler 120 by an optical fiber 122. Additionally, each optical sensor 124 in a set may have a unique characteristic, such as a unique thickness, so that the spectrometer 104 can distinguish one optical sensor 124 within a set from another optical sensor 124 within the same set. In this example, each of the four optical sensors 124 in the first set includes glass of a different thickness. In particular, each optical sensor 124 may include a coverslip of a different size, (e.g., #1, #1.5, #2, etc.). The eight sets of optical sensors 124 may be coupled to the TDM 116 by optical fibers 118 connected between the 1×4 optical couplers 120 and the TDM 116. In this example, the system 100 may include a total of thirty-two (32) optical sensors 124. Each optical sensor 124 may be configured to sense an antibody. Alternative embodiments, may include a different number of sets, and each set may include alternative numbers of optical sensors 124. In general, the system 100 may include many different configurations, each having different numbers of optical sensors 124.

In this embodiment, light from the broadband Gaussian light source 102 may be transmitted through the isolator 106, along optical fiber 108, through the 2×1 optical coupler 112, to optical fiber 114. The TDM 116 may receive the light from optical fiber 114 and communicate it in a designated time-slot to each of the sets of optical sensors 124. For example, at a first time slot, the TDM 116 may transmit the light through a first optical fiber 118 to the 1×4 coupler 120. The 1×4 coupler 120 then splits the light which then travels along each of the optical fibers 122 to each of the optical sensors 124 in the first set.

In response to receiving the light, the optical sensors 124 may each reflect at least a portion of the light back to the optical coupler 120, which combines the reflections. The reflections are then communicated to the TDM 116 along optical fiber 118. The TDM 116 passes the reflections to optical fiber 114, are communicated to the spectrometer 104 through coupler 112 and optical fiber 110. The spectrometer then detects the signals received from each of the optical sensors 124 substantially simultaneously and calculates a result corresponding to each of the individual optical sensors 124 in the first set. The spectrometer 104 may use a coherence multiplexing algorithm to separate the signals received from each optical sensor 124. In particular, the phase shift of each reflection may be a result of both the unique characteristic of the optical sensor for identifying the optical sensor as well as the amount of antibody that binds to the optical sensor. The unique characteristic, such as a unique thickness of the optical sensor may be used by the spectrometer to determine which sensor produced a each of the combined reflections.

Figure 2:
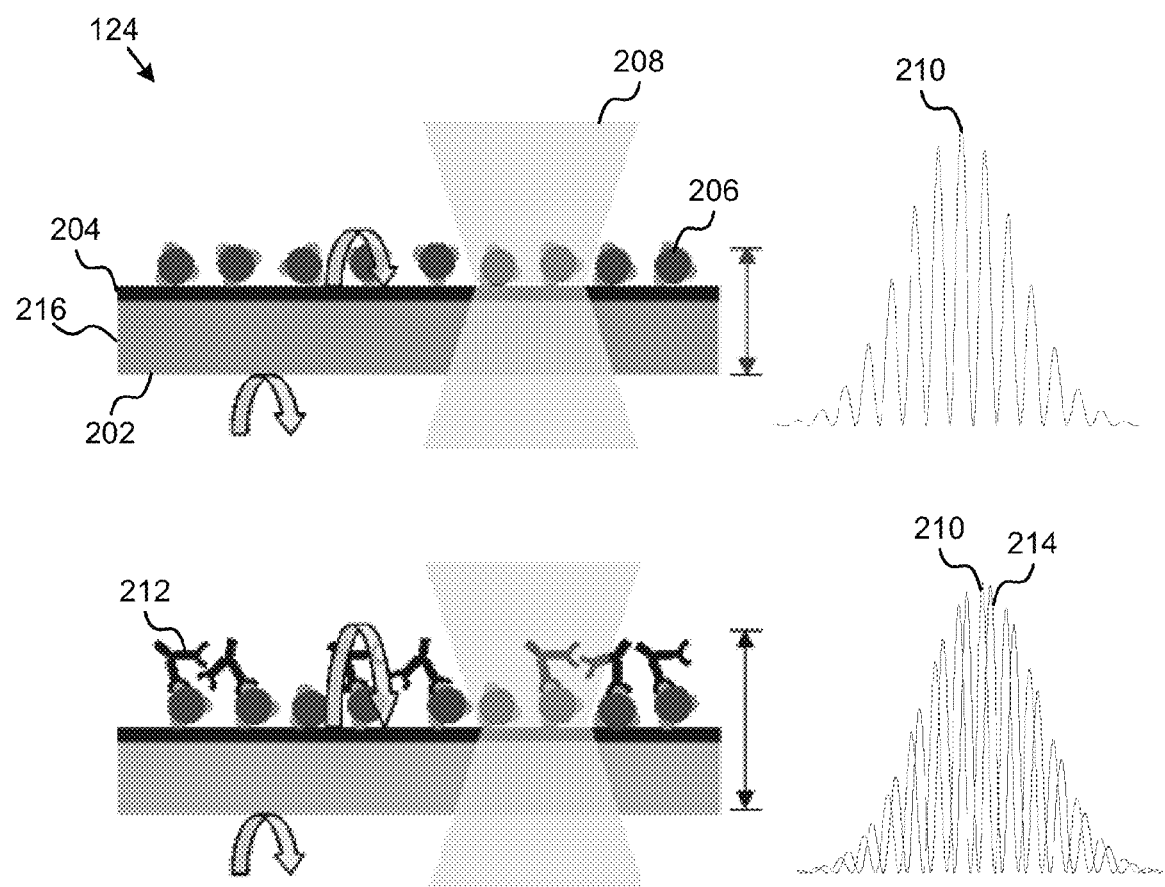
FIG. 2 is a cross-section diagram illustrating one embodiment of an optical sensor and associated sensor signals.

FIG. 2 is a cross-section diagram illustrating one embodiment of an optical sensor 124 and associated spectral interference fringe signals. A spectral interference fringe signal is formed as result of light reflecting from two surfaces of the optical sensor 124. The first surface 202 is the air-glass interface and the second surface 204 is the protein-liquid (buffer media) interface. In an alternative embodiment, the first surface 202 may be a fiber-interface surface. The fringe modulation frequency is directly proportional to the OPL between the two reflective surfaces. The top and bottom panels show reflecting surfaces of the biosensor and the corresponding spectral interference fringe signal formed before 210 and after 214 the incubation of the antibody 212. After incubation of the antibodies 212, phase of the spectral interference fringe signal shifts 214 as the OPL increases with accumulation of antibodies on the antigen functionalized surface. Light beam 208 focused on the functionalized surface interrogates binding events that occurs within the beam spot area.

In one embodiment, the optical sensor 124 may include a fiber-interface surface 202 configured to be coupled to an optical fiber 122 and to receive broadband Gaussian light 208 from the optical fiber 122. The optical sensor 124 may also include a sensor body 216 coupled to the fiber-interface surface 202, the sensor body 216 having a refractive index different from a refractive index of the optical fiber 122, such that at least a portion of light received by the fiber-interface surface 202 is reflected back to the optical fiber during use. Additionally, the sensor body 206 may be coupled to a binder-interface 204 surface. The binder-interface surface 204 may receive a chemical binder layer. For example, a molecularly tailored layer, such as an epoxy, may be deposited, on which antigens 206 may be cultured or deposited. The antigens 206 may capture antibodies of interest 212. The first spectral fringe signal 210 may correspond to the sensor with antigens 206, whereas the second spectral fringe signal 214 may correspond to the sensor with the antibody of interest captured by the antigens 206. The phase shift of the second spectral fringe signal 214 with respect to the first spectral fringe signal 210 may be directly proportional to the optical path length of the sensor with the captured antibodies 212.

One advantage of the present embodiments is that these techniques do not require use of specialized or custom designed sensors 124. Rather, any suitable optically clear material may be functionalized and used as an optical sensor. For example, a glass or plastic coverslip may be used as a sensor 124, once it has been suitably functionalized and prepared for sensing. This makes operation of the system 100 far easier and more cost effective that previously known methods.

In one example, optical configuration for detection and quantification of protein binding to the sensor 124 is a common-path interferometer 104 in which the transparent biosensor surface 202 itself is used to generate spectral interference signal. The optical setup consists of a low-coherence light source 102 (superluminescent diode, $\Delta\lambda$=20 nm, $\lambda_0$=800 nm), 2×2 single mode fiber coupler 112, and a high resolution spectrometer 104. Light from a low-coherence source 102 is input into one of the ports of the fiber coupler 112. Light after splitting at the coupler travels along the two fiber ports. In this setup only one port is utilized for biosensing. The other port can be used as another channel for detection. Light after exiting the fiber is collimated and focused on the biosensor surface 202 as illustrated in FIG. 2.

The sensors surface can be any transparent substrate with the target antigen 206 to capture the antibody of interest 212. In the spectral domain, partially coherent light reflecting from two optically separated surfaces when mixed using a interferometer produces spectral interference signal with a modulation frequency that is proportional to the optical path length difference between the two surfaces and is given by, $$S(k)=S_0(k)\{R_1+R_2+\sqrt{R_1R_2}|\mu(k)|\cos(4\pi\Delta pk)+\phi_0\} \quad (1)$$

where $s_0(k)$ is incident spectral intensity, $R_1$ and $R_2$ are reflectivities of the two surfaces, $\mu(k)$ is the spectral degree of coherence, $\Delta p$ is optical path length difference between the two surfaces and k is the wave number. In our setup $\mu(k)$ is equal to one since the light exiting the fiber is perfectly spatially coherent.

Functionalized biosensor chips used for experiments were prepared using protein capture microscope glass cover slips of various thicknesses (#1, #1.5 and #2) purchased from a commercial vendor (Xenopore Corp of Hawthorne, N.J.). These coated glass cover slips may be configured to covalently attach amino containing molecules to its surface. The reactive groups on the surface spontaneously react with primary and secondary amino groups to create a covalent bond.

In a further embodiment, the optical sensor 124 may include a Polydimethylsiloxane (PDMS) multi-well stamp. For example, Sylgard 184 Silicone elastomer (PDMS) may be supplied in two parts as lot-matched base and curing agent that are mixed in a ratio of 10 parts base to one part curing agent, by weight or volume. After mixing thoroughly, the mixture may be desiccated to get rid of any air bubbles. The mixture may then be poured on a silicon wafer and cured at 150° C. for 10 minutes. The PDMS may be peeled from the wafer, cut in size for the glass coverslips, and wells may be created using 6 mm biopsy punch. The PDMS stamp with punched holes may be cleaned using, for example, tape (e.g., SCOTCH-brand tape) and then placed on the glass coverslip. The PDMS may be pressed on the coverslip to ensure leak proof seal.

Figure 3:
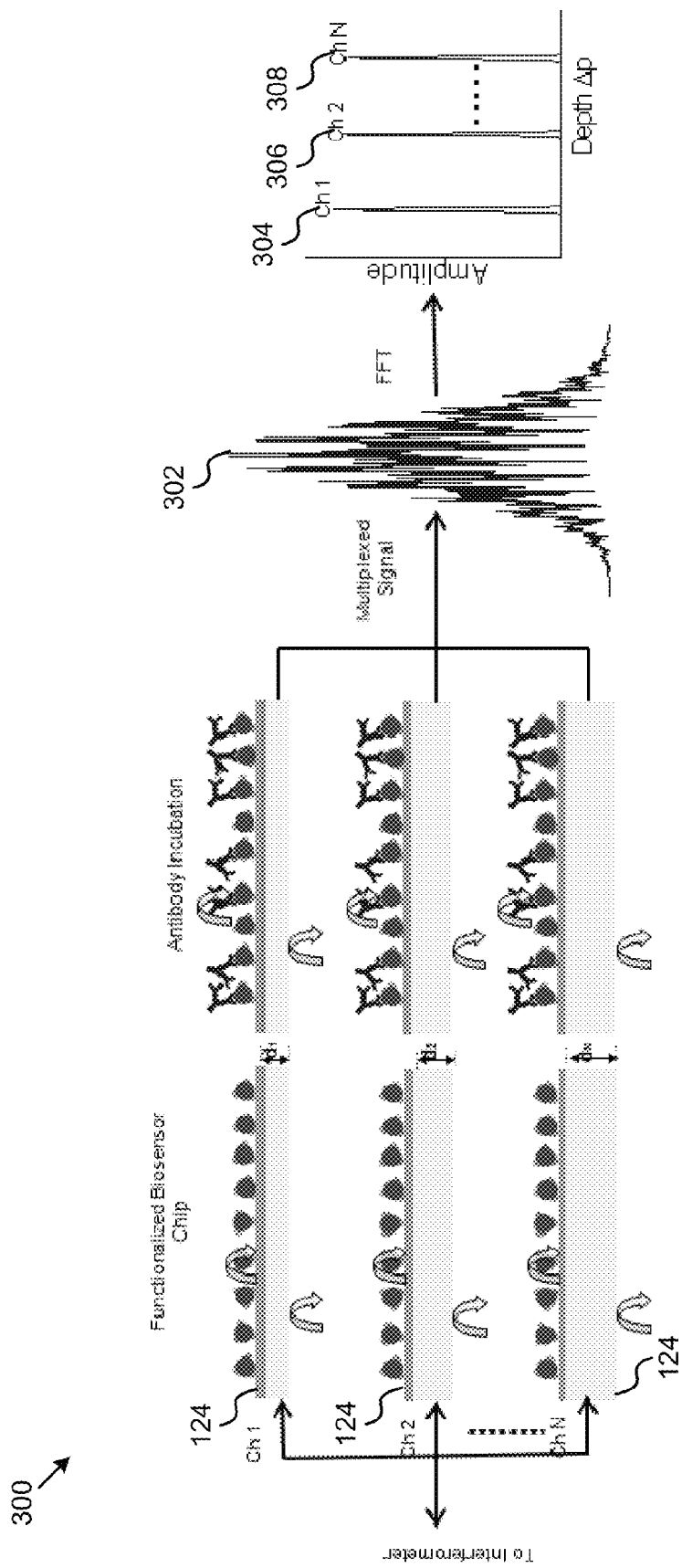
FIG. 3 is a cross-section diagram illustrating one embodiment of multiple optical sensors arranged in a coherence multiplexed arrangement and associated signals.

FIG. 3 is a cross-section diagram illustrating one embodiment of multiple optical sensors arranged in a coherence multiplexed arrangement and associated signals. In the embodiment described in FIG. 3, multiple optical sensors 124 are prepared to capture an antibody 212. The thickness of each optical sensor 124 is unique. The signals reflected by the optical sensors 124 are combined into a multiplexed signal 302. The spectrometer 102 may then transform the signals using, for example, a Fast Fourier Transform (FFT) or Hilbert transform. In such an embodiment, the transform of the signal reflected by each sensor will have a peak at a different frequency, where the frequency corresponds to a an optical path length associated with the optical sensor 124. The optical path length is determined in part by the unique thickness of the optical sensor 124, such that a first peak 304 corresponds to a signal reflected by the first optical sensor 124 on a first channel, the second peak 306 corresponds to a signal reflected by the second optical sensor 124 on a second channel, and the third peak 308 corresponds to a signal reflected by a third optical sensor 124 on a third channel.

Figure 4A:
FIG. 4A is a schematic cross-section diagram illustrating one embodiment of an optical sensor.

FIG. 4A is a schematic cross-section diagram illustrating one embodiment of a sensor unit 400. The depicted embodiment of an sensor unit 400 includes a housing 402. The housing 402 may be configured to receive at least a portion of an optical fiber 404. In one embodiment, the housing may be stainless steel. Alternatively, the housing may be aluminum, plastic, or the like. This embodiment may also include a ferrule 406 configured to retain the portion of the optical fiber 404 within the housing 402. Additionally, such embodiments may include a lens 408 disposed within the housing 402 and configured to collimate light received from the optical fiber 404 and to focus light reflected to the optical fiber 404. In a particular embodiment, the lens 408 may be a gradient-index ("GRIN") lens. Also, the sensor unit 400 may include a optical sensor 124 that can be coupled to the housing 402, the optical sensor 124 configured to reflect at least a portion of the light received from the optical fiber 404 back to the optical fiber 404. The optical sensor 124 may be integrated with the sensor unit 400 or packaged and sold separately. In a particular embodiment, the optical sensor 124 may be disposable. Alternatively, the optical sensor 124 may be reusable. In such embodiments, the optical sensor 124 may be removable from the housing for cleaning and preparation for reuse.

In a such an embodiment, the optical sensor 124 may include a fiber-interface surface 202 configured to receive broadband Gaussian light from the optical fiber 404. The optical sensor 124 may also include a sensor body 216 coupled to the fiber-interface surface 202, the sensor body 216 having a refractive index different from a refractive index of the optical fiber 404 such that at least a portion of light received by the fiber-interface surface 202 will be reflected back to the optical fiber 404 during use. Additionally, the optical sensor 124 may include a binder-interface 204 surface coupled to the sensor body 216, the binder-interface surface 204 configured to receive a chemical binder layer 206.

Figure 4B:
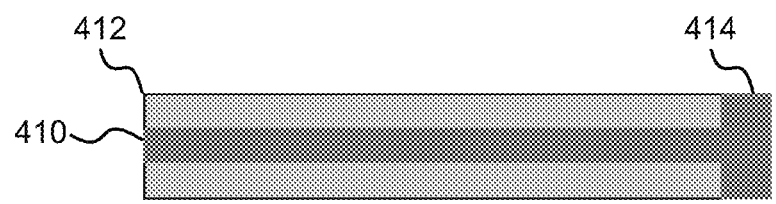
FIG. 4B is a schematic cross-section diagram illustrating one embodiment of an optical sensor.

FIG. 4B is a schematic cross-section diagram illustrating one embodiment of an optical sensor 124. In the depicted embodiment, the optical sensor includes an optical fiber having a core 410 and a cladding 412. At one end, the optical fiber may be coupled to a sapphire layer. For example, the optical fiber may be cleaved, polished, and the sapphire may be spliced to the end of optical fiber.

Figure 4C:
FIG. 4C is a schematic cross-section diagram illustrating one embodiment of an optical sensor.

FIG. 4C is a schematic cross-section diagram illustrating one embodiment of an optical sensor. In this embodiment, the optical sensor 124 includes a first segment of optical fiber 416, a partially reflective metallic layer 418, and a second segment of optical fiber 420. In one embodiment, the first segment of optical fiber 416 may be cleaved and polished. The cleaved end may then be dipped in, for example, a silver-containing solution. Alternative methods of applying the partially reflective layer may include Chemical Vapor Deposition (CVD), sputtering, painting, or the like. In such embodiments, the metallic layer 418 reflects a portion of light incident upon the layer and transmits a portion of light incident upon the sensor. The metallic layer may include silver, gold, chromium, aluminum, or other materials suitable for forming a partially reflective layer.

Figure 5:
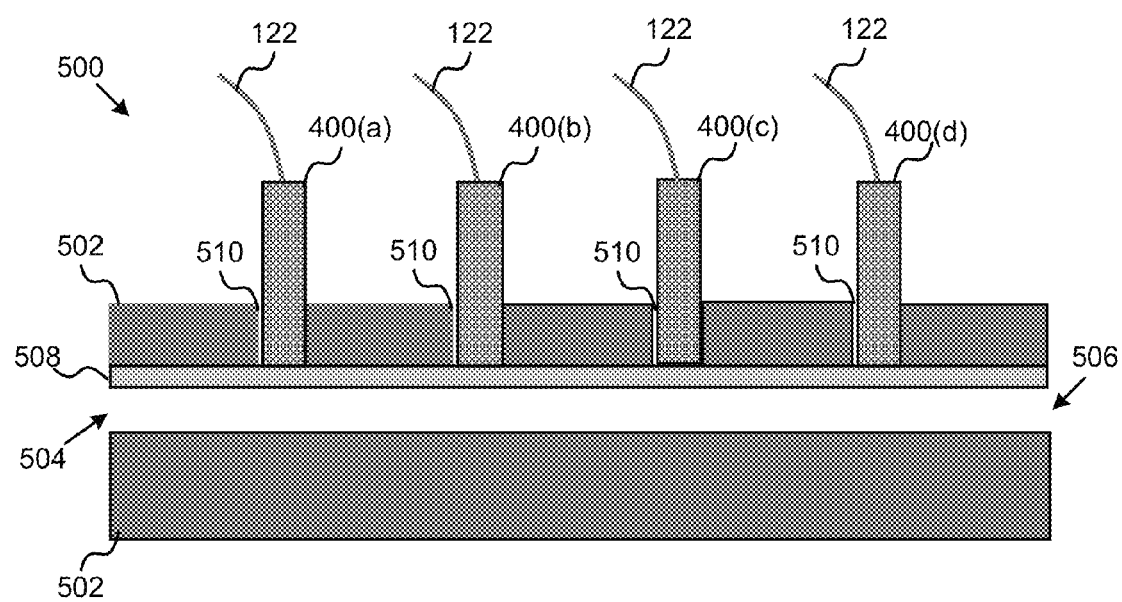
FIG. 5 is a schematic cross-section diagram illustrating one embodiment of system including multiple optical sensors arranged with reference to a flow cell.

FIG. 5 is a schematic cross-section diagram illustrating one embodiment of a system including multiple optical sensors 400 arranged with reference to a flow cell 500. In one embodiment, the flow cell 500 includes a body structure 502. The body structure 502 may include a portion defining a channel. The channel may include an inlet 504 and an outlet 506. In one embodiment, the body structure is formed of a block of DELRIN material.

In a further embodiment, an optically clear layer 508 may run adjacent the channel. For example, the optically clear layer 508 may be glass, plastic, or the like. The body structure 502 may include several portions forming a slot 510. Alternatively, these portions may be holes, grooves, or the like. The slot 510 may be configured to receive an optical sensor 124. In a further embodiment, the flow cell 500 may include multiple slots 510 for receiving multiple optical sensors 400(a)-(d).

The optical sensors 400(a)-(d) may each engage the optically clear layer 508. In one embodiment, each of the optical sensors 400(a)-(d) include an arrangement similar to that described in FIG. 4A above. In such an embodiment, however, the optical sensor element 124 may be replaced by the optically clear layer 508. The binding chemistry may be disposed within the channel on channel side of the optically clear layer 508. In an alternative embodiment, the optical sensors 400(a)-(b) may each include a sensor element 124 as described in FIG. 4A, and the optically clear layer 508 may be removed, allowing the optical sensors 400(a)-(d) direct access to the fluid in the channel.

Figure 6A:
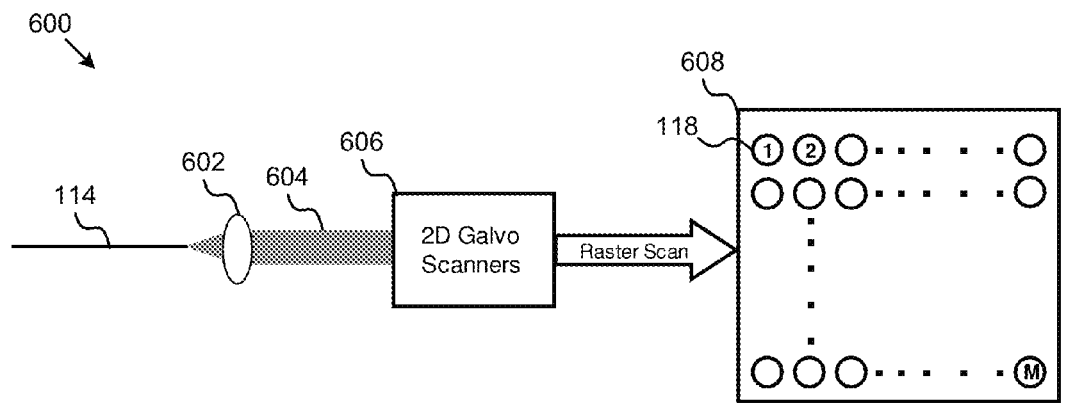
FIG. 6A is a schematic block diagram illustrating one embodiment of a system for time division multiplexing of signals received from multiple optical sensors.

FIG. 6A is a schematic block diagram illustrating one embodiment of a system for time division multiplexing of signals received from multiple optical sensors 124. In one embodiment, the TDM 116 may include an input port for receiving an optical fiber 114. Light from the optical fiber 114 may be collimated by a lens 602 into a collimated beam 604. One or more two-dimensional galvo scanners 606 may direct the beam 604 to one or more optical fibers 118. In a particular embodiment, the optical fibers may be arranged in a lanslet array 608. Alternatively, multiple fibers may be bundled and positioned to receive the beam 604 from the galvo 606. Additionally, light received from optical fibers 118 may be focused and directed back to optical fiber 114. In one embodiment, the galvo may scan the optical fibers according to a raster scan algorithm. Alternative scanning algorithms may be recognized by one of ordinary skill in the art.

Figure 6B:
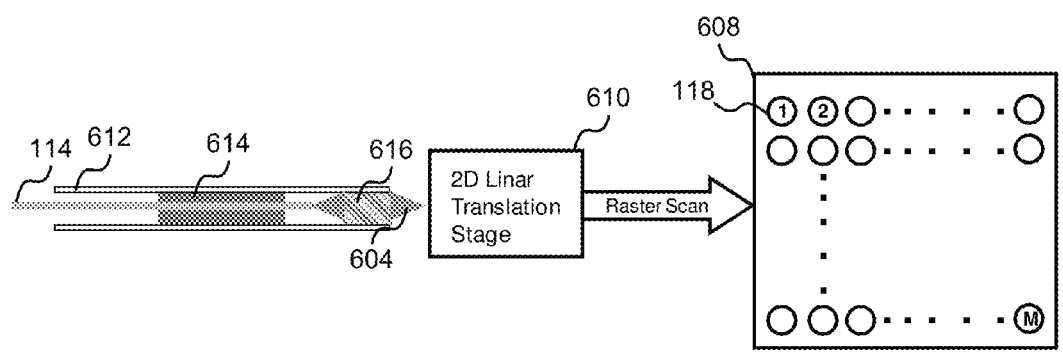
FIG. 6B is a schematic block diagram illustrating one embodiment of a system for time division multiplexing of signals received from multiple optical sensors.

FIG. 6B is a schematic block diagram illustrating another embodiment of a system for time division multiplexing of signals received from multiple optical sensors 124. In this embodiment, the fiber 114 includes a tip having a housing 612, a ferrule 614, and a lens 616. In such an embodiment, the galvo 606 may be replaced with a two-dimensional translation stage 610.

Figure 7:
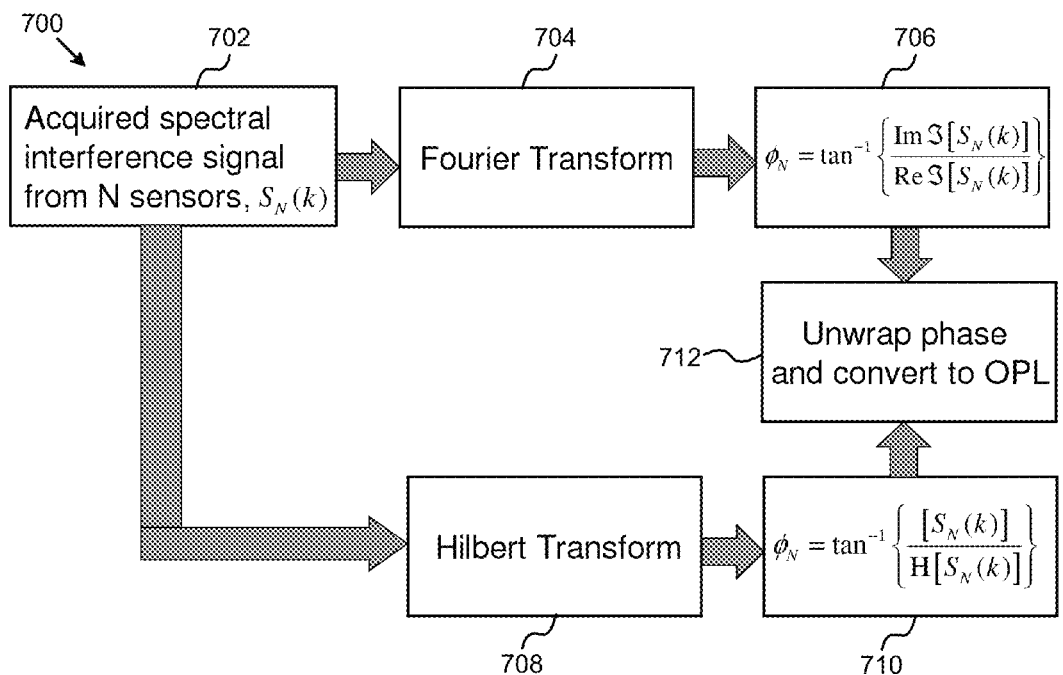
FIG. 7 is a schematic flow diagram illustrating one embodiment of a method for demultiplexing optical signals according to a coherence demultiplexing algorithm.

FIG. 7 is a schematic flow diagram illustrating one embodiment of a method 700 for demultiplexing optical signals according to a coherence demultiplexing algorithm. Method 700 includes acquiring spectral interference signals from multiple optical sensors 124. The spectral interference signals may then be transformed. In one embodiment, the signals may be transformed 704 using a Fourier transform. In such an embodiment, the phase may be determined 706 according to a calculation of the inverse tangent of the imaginary part of the Fourier transform of the signal divided by the real part of the Fourier transform of the signal as illustrated in block 706. Alternatively, the signals may be transformed using a Hilbert transform 708. In such an embodiment, the phase of the signals may be determined by calculating the inverse tangent of the signals divided by the Hilbert transform of the signals. In either case, once the phase is determined, it is unwrapped and converted to optical path length 712. Unwrapping the phase means that the phase is determined as a multiple of the period 2 π plus a remainder.

An embodiment of a system that may be used to implement the method described in FIG. 7 may include, for example, a line scan camera in the spectrometer. The line scan camera may record up to 20,000 Spectra/s. To reduce data rate for the experiments, the line scans may be externally triggered to acquire single spectra at a rate of 20 Hz. This acquisition rate may be more than sufficient for antigen-antibody binding detection experiments. The spectral data acquired by the line scan camera is digitized and transferred to a computer (not shown) for storage and processing via data acquisition card. Spectral data 702 acquired by the line scan camera in the spectrometer may be streamed to a frame grabber card, for example, National Instruments 1428, on the computer. A software module may takes the spectral data from the frame grabber card and processes it for real-time display.

An embodiment of the operation of such a software module is described in FIG. 7. For example, individual spectral scans 702 may be first converted to k-space using a spline interpolation routine and then fast Fourier transformed 704 to yield an amplitude/phase versus OPL 712.

Simultaneous interrogation of multiple sensors 124 can be achieved using frequency, wavelength or coherence domain multiplexing as described in FIG. 7. The described method uses coherence domain multiplexing for simultaneous detection of reflections from multiple optical sensors 124. In the embodiment, described in FIG. 3, each channel for sensing is a coherence separated channel with sensing information encoded in specific carrier frequency (spectral fringe frequency) that is determined by the optical thickness of the biosensor substrate. In the embodiment, a multi-channel channel interferometer is used instead of spectrometer 104 with which each channel constitutes an independent common path interferometer interrogates the various optical sensors 124.

A representation of the combined spectral interferometric fringe signal from multiple optical sensors 124 detected by the spectrometer 104 may be represented as, $$S(k) = \alpha S_0(k) \left\{ R_1 + R_2 + \sqrt{R_1 R_2} |\mu(k)| \sum_{m=1}^{N} \cos(4\pi \Delta p_m k) \right\} \quad (2)$$

where $S_0(k)$ is incident spectral intensity, $R_1$ and $R_2$ are reflectivities at the two biosensor interface surfaces responsible for the generating the biosensing signal, $\mu(k)$ is the spectral degree of coherence, $\Delta p_m$ is optical path length difference between the two surfaces of the $m^{th}$ biosensor, k is the wave number, $\alpha$ is the fraction of light reflected from individual biosensor that is coupled into the spectrometer.

The modulation frequency of the spectral fringes may be directly proportional to the thickness of the biosensor surface. The spectral resolution of the spectrometer may be, for example, 0.1 nm which dictates the max difference in OPL that can be measured by that particular spectrometer 104, and hence the max thickness of the transparent substrate (1.5 mm, for glass of refractive index of 1.45) that can be used as an optical sensor 124. The bandwidth of the low coherence source may determine the smallest thickness of the transparent substrate that can be used as a biosensor surface.

The optical sensor 124 may be any transparent substrate functionalized to capture an antibody of interest. In the spectral domain, partially coherent light reflecting from two optically separated surfaces when mixed using a interferometer produces spectral interference signal with a modulation frequency that is proportional to the optical path length difference between the two surfaces.

In one embodiment of the process of FIG. 7, the Fourier transform 704 of the acquired signals 702 may be taken. Fourier transformation of eq. 1 yields the magnitude of reflected signal as a function of OPL separation between the reflecting surfaces. Assuming a Gaussian source, Fourier transformation yields a Gaussian function with the peak centered at Δp and the width proportional to the bandwidth of the low coherence source. As illustrated in FIG. 2, spectral interference fringe signal may be formed as a result of light reflecting from two surfaces of the biosensor as indicated by arrows in top and bottom panels. Binding of antibodies 212 to antigen 206 functionalized surface 204 may result in sub-wavelength changes in OPL which results in phase shift of the spectral interference fringe signal 214. In one example embodiment, the spectrometer 104 is a high speed spectrometer capable of acquiring 20 K spectra/sec with a resolution of 0.1 nm. For detection of sub-wavelength change in OPL, the phase of the spectral fringe signal may be measured, which can be found by the following expression, $$\phi = \tan^{-1}\left\{\frac{\text{Im}\mathcal{J}[S(k)]}{\text{Re}\mathcal{J}[S(k)]}\right\}\bigg|_{z=\Delta p} = \frac{4\pi\Delta p}{\lambda_0} \quad (3)$$

where $\lambda_0$ is center wavelength of the low coherence source. In one embodiment, the low-coherence source has a symmetrical spectrum.

The total phase change is proportional to the number of antibody molecules 212 binding to the antigen 206 per unit area. Formation of a complete antibody monolayer bound to the antigen layer 206 represents the maximum detectable concentration of antibodies 212. The minimum number of antibodies 212 that can be detected and quantified depends on the phase sensitivity of the technique and morphology (shape and size) of the antibody 212. The adsorbed mass per unit area of bound antibodies can be quantified as, $$\eta = \frac{\phi_m}{\phi_T} \times \frac{w_m}{A_m} \quad [\text{ng/mm}^2] \quad (4)$$

where $\phi_m$ is phase change due to a given concentration of incubated antibody, $\phi_T$ is total phase change due to saturation coverage of the bound antibody, $w_m$ is weight of the antibody molecule and $A_m$ is the cross-section area of the antibody molecule orthogonal to the incident optical probe beam axis. The configuration in which the antibody attaches to the antigen will determine the cross-sectional area. Ultimately, the value of $\phi_T$ may be determined by the density of available sites for antibody binding and morphology of the antibody. The lower limit of adsorbed mass detection may depend on the phase noise ($\phi_m = \phi_{noise}$) of the interferometer 104 for a given optical sensor 124.

Other embodiments may include optical sensors 124 configured to detect other target materials, such as analytes. One of ordinary skill in the art will recognize a variety of chemical methods for functionalizing an optical sensor 124 for detection of a variety of chemicals and molecules.

Figure 8:
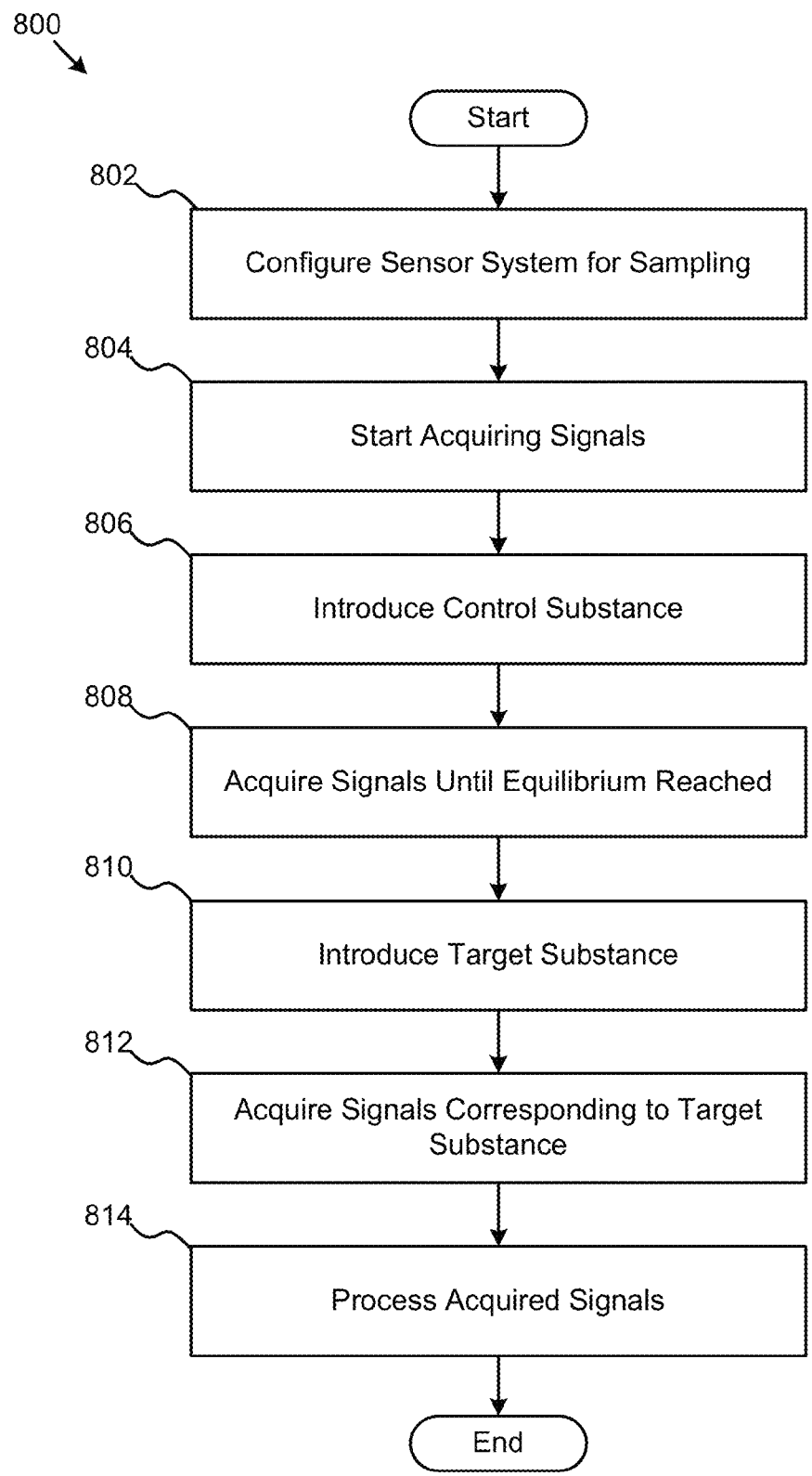
FIG. 8 is a schematic flowchart diagram illustrating one embodiment of a method for label-free quantitative detection of bio-markers.

FIG. 8 is a schematic flowchart diagram illustrating one embodiment of a method 800 for quantitative detection of bio-markers. In one embodiment, the method 800 starts by configuring 802 a sensor system 100 for sampling. This may include providing one or more optical sensors, connecting the system components, and chemically preparing the optical sensor to detect a target molecule.

Then, according to one embodiment of the method 800, the system 100 may start 804 acquiring signals. For example, a spectrometer 104 may start 804 acquiring signals from multiple optical sensors 124. A control substance may then be introduced 806 for acquisition of baseline signals. In one embodiment, the control substance may be a buffer solution that does not contain an antibody of interest. The spectrometer 104 may continue to acquire 808 signals until an equilibrium state is reached, indicating that a baseline signal has been captured that is sufficient for analysis of the target substance.

According to one embodiment, the target substance may then be introduced 810. For example, a buffer solution containing the an antibody or analyte of interest may be introduced 810 to the optical sensors 124, through, for example, a flow cell 500. The spectrometer 104 may continue to acquire 812 signals corresponding to the target substance, and a computer or processing device may process 814 the acquired signals to quantify, for example, an amount of the target substance sensed by the optical sensor 124.

Figure 9:
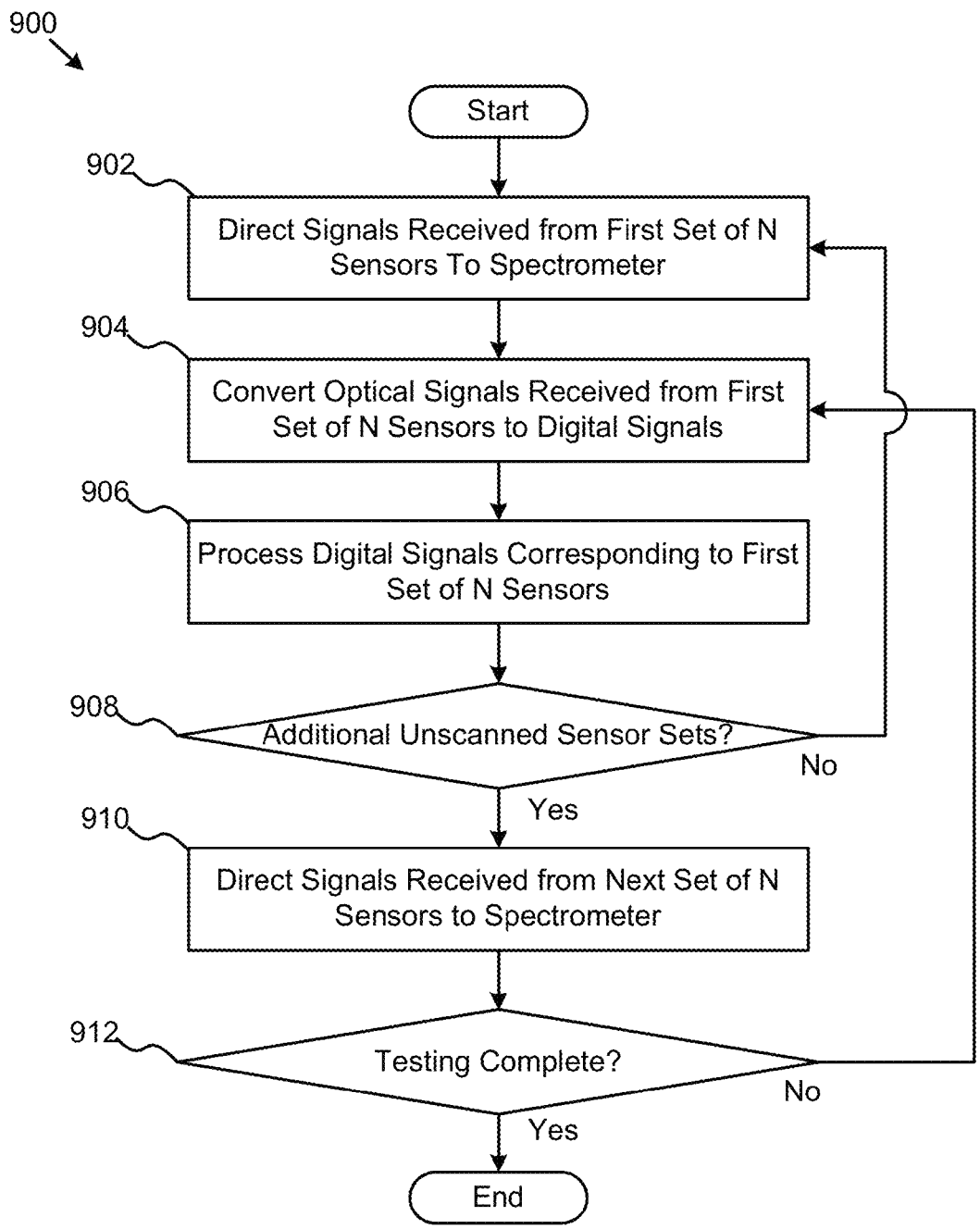
FIG. 9 is a schematic flowchart diagram illustrating one embodiment of a method for operating a multiplexed system according to present embodiments.

FIG. 9 is a schematic flowchart diagram illustrating one embodiment of a method 900 for operating a multiplexed system according to the present embodiments. In one embodiment, the method 900 starts with directing 902 signals received from a first set of optical sensors 124 to the spectrometer 104. For example, a TDM 116 comprising a galvo scanner 606 may be used to direct 902 signals from a first optical fiber 118 to a second optical fiber 114, where the optical fiber is coupled to the spectrometer 104.

The spectrometer 104 may then convert 904 the optical signals received from the first set of optical sensors 124 to digital signals. The spectrometer 104, or an associated computer or processing device, may then process 906 the digital signals corresponding to the first set of optical sensors 124. Processing 906, may include transforming the results according to a Fourier transform 704, a Hilbert transform 708, or the like. Processing 906 may also include performing one or more calculations on digital representations of the signals and the transforms as described in FIG. 7. Processing 906 may also include determining an optical path length, or otherwise quantifying an amount of a target substance detected by each of the optical sensors 124. In a particular embodiment, processing may include determining which portion of the acquired signal corresponds to a particular one of the optical sensors 124 in the set. For example, each optical sensor 124 may have a unique characteristic, such as a unique thickness. Processing may include performing coherence domain demultiplexing by identifying which sensor 124 reflected a transformed peak based on the optical path length. One example of this processing is illustrated in FIG. 3.

If the TDM 116 determines 908 that additional unscanned sets exist, it may direct 910 the galvo to a next set of sensors in a sequence of sets. For example, the TDM 116 may perform a raster scan of the sets. If, however, all of the sets have been scanned the TDM 116 may repeat the process until a determination 912 is made that testing is complete.

EXAMPLES

Figure 10:
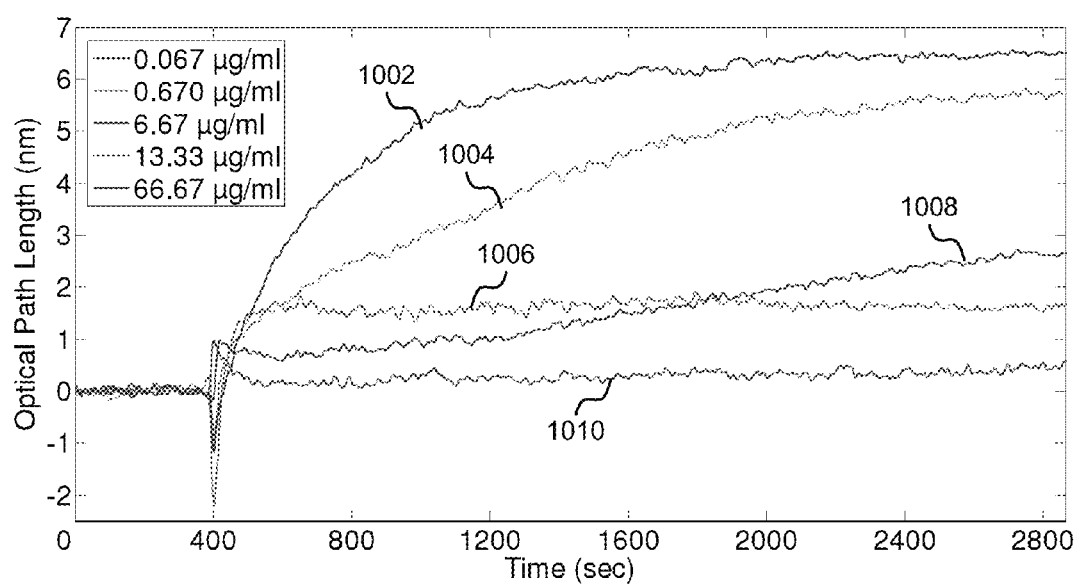
FIG. 10 is a graphical illustration of a quantitative measurement of optical path length with respect to time produced by an embodiment of apparatuses, systems, and methods.

FIG. 10 is a graphical illustration of a quantitative measurement of optical path length with respect to time produced by an embodiment of the system 100. FIG. 10 represents a dynamic change in OPL with anti-rabbit IgG (antibody) binding to rabbit IgG (antigen) layer for different concentrations of the antibody. Commercially available ordinary glass coverslips coated with protein capture surfaces were purchased and functionalized with the antigen. In brief, coated glass coverslips were thoroughly washed and a Polydimethylsiloxane (PDMS) stamp with several punched holes is placed on the coverslip to yield a multi-well (60 µl) plate for conducting the binding experiments. Wells were incubated with IgG (2 mg/ml) and stored at 4° C. for 12 hrs after which they were washed (3×) with 0.1% Tween-PBS and PBS separately. After washing the wells were filled with PBS and stored in the refrigerator. Before starting the experiments multi-well the optical sensor 112 chip was removed from the refrigerator and allowed to equilibrate to room temperature. The optical sensor 112 was then placed on a tip-tilt mirror mount attached to a translation stage. The sensor surface is positioned such that the probe beam focus is at the glass-liquid (buffer) interface. Wells were first incubated with 20 µl of PBS and data acquisition is initiated. After a fixed interval of time wells were incubated with IgG antibodies via a pipette. Change in OPL that occurred as a function of time for various concentration IgG antibody binding to functionalized antigen layer is shown in FIG. 10. Curve 1002 corresponds to a concentration of 66.67 µg/ml, curve 1004 corresponds to a concentration 13.33 µg/ml, curve 1006 corresponds to a concentration of 6.67 µg/ml, curve 1008 corresponds to a concentration of 0.670 µg/ml, curve 1010 corresponds to a concentration of 0.067 µg/ml. Spectral fringes were recorded every 50 ms. For the plots in FIG. 10 the measured phase was averaged for an interval period of one second. The transient seen at the onset of IgG incubation is an artifact that was caused by liquid dropping in to the well from the pipette and mechanically perturbing the sensor. This transient does not affect the final quantification of the OPL.

Figure 11:
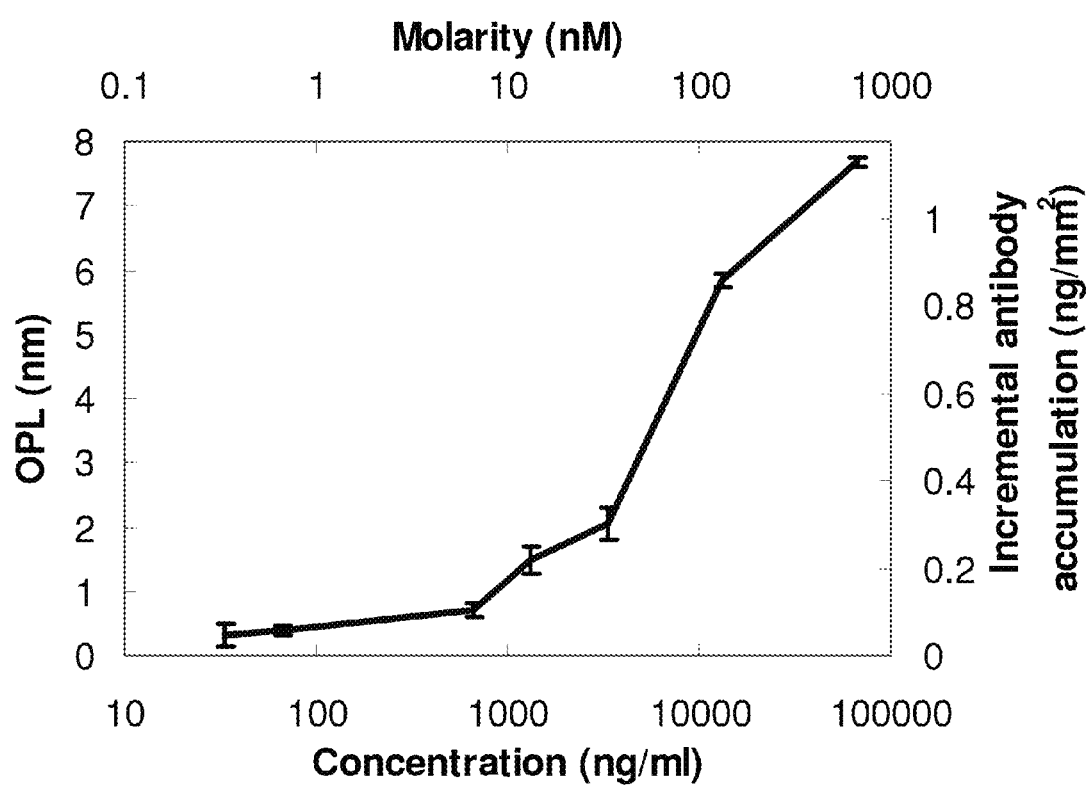
FIG. 11 is a graphical illustration of a quantitative measurement of optical path length, concentration of an antibody in a target sample, incremental antibody accumulation, and molarity of the antibody in the liquid.

Direct attachment of the fiber probe to the sensor or a flow cell configuration may eliminate the transient phase perturbation. In this static flow setup the IgG molecules may reach the antigen surface primarily through diffusion and Brownian motion. IgG antibody concentration ranging from 220 pM to 440 nM which represents a mass coverage of 0.05 ng/mm$^2$ to 1.18 ng/mm$^2$ were detected with the phase sensitive spectral domain interferometric technique. FIG. 11 describes these results. In particular, FIG. 11 illustrates a change in OPL and incremental mass coverage due to binding of antibodies to the surface immobilized antigen as function of anti-rabbit IgG (antibody) concentration. Change in OPL with reference to concentration is represented on the left y-axis whereas the equivalent mass coverage of IgG is quantified on the right y-axis. In calculating the mass coverage protein binding site density of 2.5 ng/mm$^2$ (as per the manufacturer) was used. Furthermore the cross-sectional area for the IgG antibody was calculated to be $3.14 \times 10^{-12}$ mm$^2$ assuming IgG antibody to be of an ellipsoidal shape oriented along its major axis when bound to the antigen. The measured sensitivity of detecting IgG antibodies was 33 ng/ml from a single detection spot. The antibody mass coverage was a linear function of IgG antibody concentration up to 100 nM after which it begins to saturate and shows nonlinear dependence.

Figure 12:
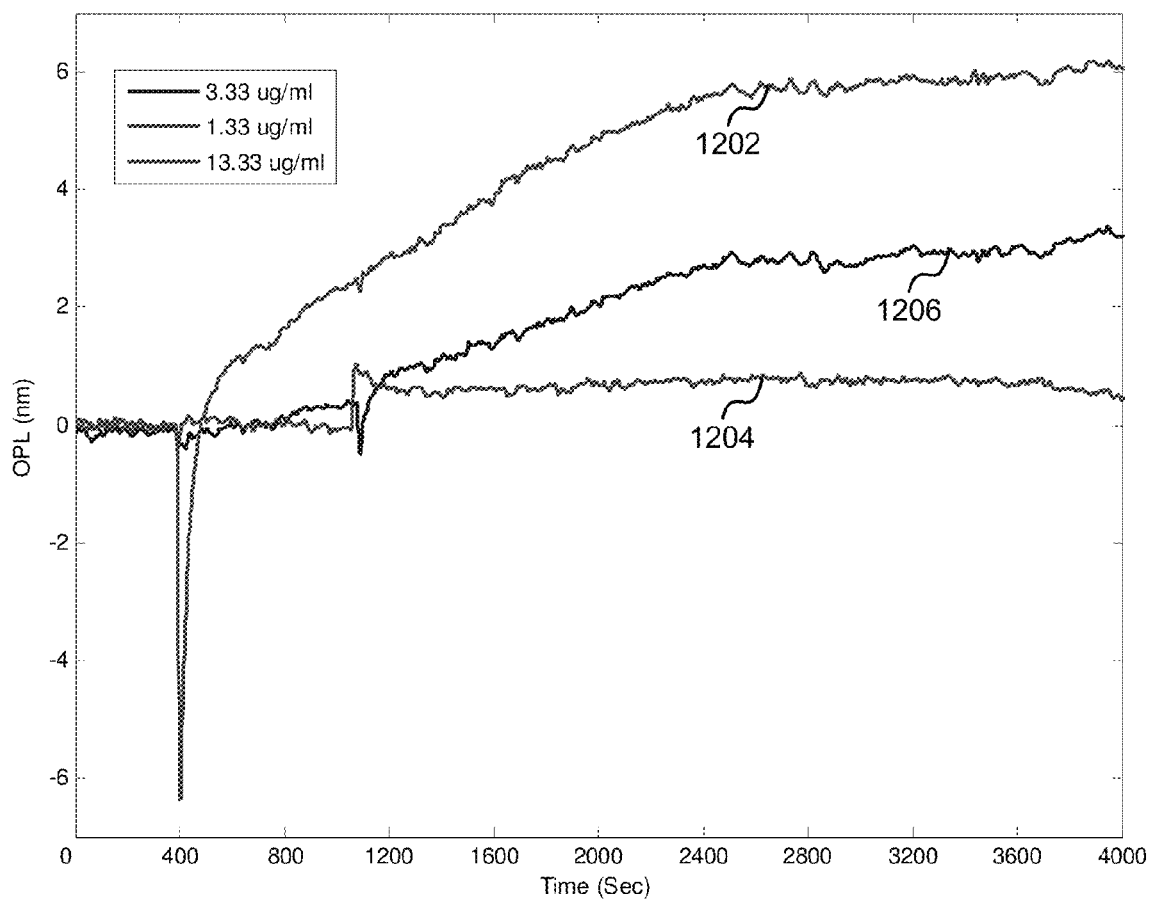
FIG. 12 is a graphical illustration of a quantitative measurement of optical path length with respect to time for each of multiple optical sensors in a multiplexed system according to present embodiments.

FIG. 12 is a graphical illustration of a quantitative measurement of optical path length with respect to time for each of multiple optical sensors in a multiplexed system according to the present embodiments. Three surfaces of different thickness (glass coverslip #1, #1.5, #2) were used as sensors to demonstrate the principle of coherence division multiplexing. Each sensor was functionalized with IgG (antigen) which is the capture molecule for IgG antibodies. Shown in FIG. 12 is biomolecular interaction analysis of IgG antibodies binding to IgG immobilized on the sensors surfaces of various thicknesses. Each sensor 124 generated a spectral interference of a fixed modulation frequency proportional to its optical thickness giving rise to a unique peak (channel) in the Fourier transformed signals. The phase of each channel was measured. Spectrum was acquired at an time interval of 50 ms. Phase converted to OPL is plotted as a function of time showing the simultaneous binding of anti IgG to IgG at three different sensor surfaces demonstrating detection of multiple biomolecular interactions using the principle of coherence division multiplexing.

All of the methods disclosed and claimed herein can be made and executed without undue experimentation in light of the present disclosure. While the apparatus and methods of this invention have been described in terms of preferred embodiments, it will be apparent to those of skill in the art that variations may be applied to the methods and in the steps or in the sequence of steps of the method described herein without departing from the concept, spirit and scope of the invention. For example, one of ordinary skill in the art will recognize a wide variety of sensor materials, thicknesses, and geometries. Additionally, one of ordinary skill in the art will recognize a wide variety of chemistry schemes for functionalizing the sensors. In addition, modifications may be made to the disclosed apparatus and components may be eliminated or substituted for the components described herein where the same or similar results would be achieved. For example, certain optical fiber paths, optical couplers, or the like may be eliminated depending upon system implementation. All such similar substitutes and modifications apparent to those skilled in the art are deemed to be within the spirit, scope, and concept of the invention as defined by the appended claims.

What is claimed is:

1. A system comprising:
    a light source configured to emit broadband Gaussian light;
    an optical fiber interferometer comprising:
        an optical fiber coupled to the light source; and
        an optical sensor comprising:
            a fiber-interface surface configured to be coupled to the optical fiber to receive broadband Gaussian light;
            a sensor body coupled to the fiber-interface surface such that at least a portion of light received by the fiber-interface surface will be reflected back to the optical fiber during use; and
            a binder-interface surface coupled to the sensor body, the binder-interface surface configurable to receive a chemical binder layer; and
    a high-resolution spectrometer coupled to the optical fiber interferometer to receive light reflected by the optical sensor, the spectrometer configured to detect interference between (i) light reflected from the fiber-interface surface of the optical sensor and (ii) light reflected from the binder-interface surface of the optical sensor.

2. The system of claim 1, comprising a 1 xN optical coupler having N channels, each of the N channels configured to direct the light reflected by a different optical sensors to the spectrometer.

3. The system of claim 2, further comprising;
    M number of branches, each branch having a 1 xN optical coupler with N channels; and
    a multiplexer configured to communicate light reflected by a plurality of optical sensors to the spectrometer.

4. The system of claim 3, where the multiplexer comprises a time division multiplexer (TDM).

5. The system of claim 4, where the multiplexer comprises a galvo configured to temporally scan each of the M branches.

6. The system of claim 2, where the multiplexer is configured to apply a coherence de-multiplexing algorithm identify signals from each of a plurality of optical fiber interferometers, each coupled to a different one of the N channels.

7. The system of claim 1, comprising:
    one or more sets of optical fiber interferometers each comprising an optical fiber and an optical sensor coupled to the optical fiber, at least a first where each optical sensor of a first set having a unique physical thickness;
    where the spectrometer is coupled to the plurality of optical fiber interferometers, the spectrometer configured to simultaneously detect light reflected by each optical sensor in the first set of optical fiber interferometers, and demultiplex the signals received according to a coherence multiplexing algorithm.

8. The system of claim 7, comprising a TDM coupled to the one or more sets of optical sensors, the TDM configured to communicate light reflected by the each of the sets of optical sensors to the spectrometer within a designated time slot.

9. The system of claim 1, comprising a flow cell coupled to the optical sensor, the flow cell configured to direct target materials into contact with the optical sensor.

10. The system of claim 1, where the optical sensor is separated from the optical fiber by a gap.

11. The system of claim 1, where the optical sensor is separated from the optical fiber by a lens.

12. The system of claim 1, where the chemical binder layer comprises a molecularly tailored capture layer.

* * * * *

UNITED STATES PATENT AND TRADEMARK OFFICE
CERTIFICATE OF CORRECTION

PATENT NO. : 8,617,470 B2
APPLICATION NO. : 12/943925
DATED : December 31, 2013
INVENTOR(S) : Digant P. Davé

Page 1 of 1

It is certified that error appears in the above-identified patent and that said Letters Patent is hereby corrected as shown below:

In the Claims

In claim 2 on column 16, line 40, "1 xN" should read --1xN--.

In claim 2 on column 16, line 42, delete "sensors" and insert --sensor-- therefor.

In claim 3 on column 16, line 45, "1 xN" should read --1xN--.

In claim 6 on column 16, line 54, insert --to-- between "algorithm" and "identify".

Signed and Sealed this
Eighth Day of April, 2014

Michelle K. Lee
*Deputy Director of the United States Patent and Trademark Office*